(12) United States Patent
Wu et al.

(10) Patent No.: US 10,501,779 B2
(45) Date of Patent: Dec. 10, 2019

(54) OLIGONUCLEOTIDE TRAPPING

(75) Inventors: Chao-ting Wu, Brookline, MA (US); Brian Beliveau, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 13/469,242

(22) Filed: May 11, 2012

(65) Prior Publication Data
US 2013/0143208 A1 Jun. 6, 2013

Related U.S. Application Data

(60) Provisional application No. 61/485,170, filed on May 12, 2011.

(51) Int. Cl.
| | |
|---|---|
| *C12Q 1/68* | (2018.01) |
| *C12Q 1/6841* | (2018.01) |
| *G01N 33/53* | (2006.01) |
| *G01N 33/50* | (2006.01) |
| *G01N 33/58* | (2006.01) |

(52) U.S. Cl.
CPC ............ *C12Q 1/6841* (2013.01); *G01N 33/50* (2013.01); *G01N 33/53* (2013.01); *G01N 33/58* (2013.01); *G01N 2458/10* (2013.01)

(58) Field of Classification Search
CPC ............ C12Q 2525/313; C12Q 1/6886; C12Q 1/682; C12Q 2600/136; C12Q 2600/158; C12Q 2537/143; C12Q 1/6837; C12Q 1/6806; C12Q 2537/125; C12Q 1/6816; C12Q 1/6834; C12Q 1/6883; C12Q 2600/106; C12Q 2600/156; C12Q 2525/113
USPC .......... 435/6.1, 6.11, 7.1, 91.1; 436/94, 501; 536/23.1, 24.3, 24.33; 530/300, 350
See application file for complete search history.

(56) References Cited

U.S. PATENT DOCUMENTS

| | | | |
|---|---|---|---|
| 5,447,841 A | 9/1995 | Gray et al. | |
| 5,635,400 A | 6/1997 | Brenner | |
| 5,981,179 A | 11/1999 | Lorinez et al. | |
| 6,066,459 A | 5/2000 | Garini et al. | |
| 2001/0004728 A1* | 6/2001 | Preparata ............ | C12Q 1/6874 702/20 |
| 2002/0081588 A1* | 6/2002 | De Lumley-woodyear et al. ....... | 435/6 |
| 2003/0170675 A1* | 9/2003 | Xiang et al. ....................... | 435/6 |
| 2005/0033520 A1* | 2/2005 | Dai et al. ......................... | 702/19 |
| 2007/0088014 A1* | 4/2007 | Edelman .............. | A61K 9/0048 514/179 |
| 2008/0206787 A1* | 8/2008 | Wu et al. ......................... | 435/7.4 |
| 2010/0304994 A1 | 12/2010 | Wu et al. | |

FOREIGN PATENT DOCUMENTS

EP 0799897 A1 10/1997

OTHER PUBLICATIONS

Anglana, et al., "Construction of a Recombinant Adenovirus for Efficient Delivery of the I-SceI Yeast Endonuclease to Human Cells and its Application in the In Vivo Cleavage of Chromosomes to Expose New Potential Telomeres", Nucleic Acids Research, 1999, pp. 4276-4281, vol. 27, Oxford University Press.
Bayani, et al., "Multi-Color FISH Techniques", Current Protocols in Cell Biology, 2004, pp. 22.5.1-22.5.25, Suppl. 24, John Wiley & Sons, Inc.
Brenner, et al., "In Vitro Cloning of Complex Mixtures of DNA on Microbeads: Physical Separation of Differentially Expressed cDNAs", PNAS, Feb. 15, 2000, pp. 1665-1670, vol. 97.
Carter, et al., "Long-Range Chromatin Regulatory Interactions In Vivo", Nature Genetics, Dec. 2002, pp. 623-626, vol. 32.
Danilova, et al., "Integrated Cytogenetic Map of Mitotic Metaphase Chromosome 9 of Maize: Resolution, Sensitivity, and Banding Paint Development", Chromosoma, 2008, pp. 345-356, vol. 117.
Dejardin, et al., "Purification of Proteins Associated with Specific Genomic Loci", Cell, Jan. 9, 2009, pp. 175-186, vol. 136, Elsevier, Inc.
Fransz, et al., "Interphase Chromosomes in *Arabidopsis* are Organized as Well Defined Chromocenters from which Euchromatin Loops Emanate", PNAS, Oct. 29, 2002, pp. 14584-14589, vol. 99.
Gall, et al., "Nucleic Acid Hybridization in Cytological Preparations", Meth. Enzymol., 1981, pp. 470-480.
Goodwin, et al., "Rapid Sizing of Individual Fluorescently Stained DNA Fragments by Flow of Cytometry", Nucleic Acids Research, 1993, pp. 803-806, vol. 21.
Gruen, et al., "An In Vivo Selection System for Homing Endonuclease Activity", Nucleic Acids Research, 2002, pp. 1-6, vol. 7, Oxford University Press.
Henderson, Ann, "Cytological Hybridization to Mammalian Chromosomes", International Review of Cytology, 1982, pp. 1-41. vol. 76, Academic Press, Inc.
Lowenstein, et al., "Long-Range Interphase Chromosome Organization in *Drosophila*: A Study Using Color Barcoded Fluorescence In Situ Hybridization and Structural Clustering Analysis", 2004, Mol. Biol. Cell, pp. 5678-5692, vol. 15, The American Society for Cell Biology.
Ried, et al., "Simultaneous Visualization of Seven Different DNA Probes by In Situ Hybridization Using Combinatorial Fluorescence and Digital Imaging Microscopy", 1992, Proc. Natl. Acad. Sci. USA, pp. 1388-1392, vol. 89.
Roberts, et al., "Novel Method for the Production of Multiple Colour Chromosome Paints for Use in Karotyping by Fluorescence In Situ Hybridisation", Genes, Chromosomes & Cancer, 1999, pp. 241-250, vol. 25.
Schrock, et al., "Multicolor Spectral Karotyping of Human Chromosomes", Science, 1996, pp. 494-497, vol. 273.
Shoemaker, et al., "Quantitative Phenotypic Analysis of Yeast Deletion Mutants Using a Highly Parallel Molecular Bar-Coding Strategy", Nature Genetics, Dec. 14, 1996, pp. 450-456, vol. 14.

(Continued)

*Primary Examiner* — Frank W Lu
(74) *Attorney, Agent, or Firm* — Banner & Witcoff, Ltd.

(57) ABSTRACT

Novel methods and compositions for identifying one or more factors associated with a nucleic acid sequence (e.g., DNA and/or RNA) of interest are provided.

26 Claims, 4 Drawing Sheets

(56) References Cited

OTHER PUBLICATIONS

Speicher, et al., "Karyotyping Human Chromosomes by Combinatorial Mulit-Fluor FISH", Nature Genetics, 1996, pp. 368-375, vol. 12.

Suchanek, et al., "Photo-Leucine and Photo-Methionine Allow Identification of Protein-Protein Interactions in Living Cells", Nature Methods, 2005, pp. 1-7, Advance Online Publication.

* cited by examiner

OLIGONUCLEOTIDE TRAPPING

RELATED APPLICATION DATA

This application claims priority to U.S. Provisional Patent Application No. 61/485,170, filed on May 12, 2011 and is hereby incorporated herein by reference in its entirety for all purposes.

STATEMENT OF GOVERNMENT INTERESTS

This invention was made with Government support under the National Institutes of Health grant number GM085169-01A1. The Government has certain rights in the invention.

FIELD

Embodiments of the present invention relate in general methods for characterizing chromosome-associated factors.

BACKGROUND

Gene activity, chromosome behavior, and essentially all DNA-based genetic function depend to some extent on the factors that are associated with DNA. Hence, understanding of genetic function and the application of this understanding to medical or other needs calls for the identification of such factors, which can be nucleic acid, protein, lipid, or essentially of any chemical compound. Currently, technologies for the identification of such factors are limited by expense of the approach and, in part a consequence of this, the constraint to focus primarily on highly repeated regions of the genome.

SUMMARY

The present invention is based in part on the discovery of methods and compositions useful for identifying and/or characterizing factors that associate with, modify or otherwise interact with nucleic acid sequences (e.g., DNA (e.g., nuclear, mitochondrial, transfected and the like) and/or RNA). The present invention provides facile methods for targeting specific, single copy or low copy number regions of the nuclear and mitochondrial genomes and/or transfected and other DNAs. Such methods can be further adapted to target RNA and the factors that associate with and regulate RNA activities.

Accordingly, in certain exemplary embodiments, methods for identifying one or more factors associated with a nucleic acid sequence of interest (e.g., genomic, chromosomal or transfected DNA and/or RNA) are provided. The methods include the steps of providing a biological sample including a nucleic acid sequence of interest, contacting the biological sample with a plurality of oligonucleotide paints, wherein the oligonucleotide paints include a targeting moiety, and wherein substantially all of the oligonucleotide paints have a unique nucleotide sequence relative to one another, allowing the oligonucleotide paints to bind to the nucleic acid sequence of interest, allowing the targeting moiety to bind to the one or more factors, and identifying the one or more factors bound to the targeting moieties of the oligonucleotide paints.

In certain aspects, the methods further include the step of retrieving the oligonucleotide paints prior to the step of identifying. In certain aspects, the oligonucleotide paints further include retrievable moieties, e.g., one component of a binding pair such as, for example, biotin-streptavidin. In other aspects, the oligonucleotide paints are retrieved by binding the retrievable moieties. In yet other aspects, the targeting moiety is inert until activation, e.g., by heat activation, light activation, chemical activation and any combination of these. In certain aspects, the targeting moieties bind a protein, a peptide, a carbohydrate, a lipid, a chemical moiety (e.g., a methyl group or an acetyl group or the like) or any combination of these. In still other aspects, the one or more factors include nucleic acid sequences (e.g., DNA and/or RNA), polypeptides (e.g., of one or more histone proteins, scaffold proteins, transcription factors, DNA binding proteins, DNA repair factors, nucleases and the like), carbohydrates, lipids, chemical moieties and the like and any combination of these. In certain aspects, the methods include the use of a set of oligonucleotide paints to identify factors associated with a plurality of nucleic acid sequences of interest, e.g., at least 50, 100, 1000 or more nucleic acid sequences of interest. In other aspects, the nucleic acid sequence of interest is chromosomal DNA, e.g., present in a single copy, in low copy numbers, in moderately repetitive elements or in highly repetitive elements.

In other exemplary embodiments, methods for identifying one or more factors associated with genomic (e.g., chromosomal, mitochondrial, etc.) DNA are provided. The methods include the steps of providing a biological sample including genomic (e.g., chromosomal, mitochondrial, etc.) DNA, contacting the biological sample with a plurality of oligonucleotide paints, wherein the oligonucleotide paints include a targeting moiety, and wherein substantially all of the oligonucleotide paints have a unique nucleotide sequence relative to one another, allowing the oligonucleotide paints to bind to the genomic (e.g., chromosomal, mitochondrial, etc.) DNA, allowing the targeting moieties to bind to the one or more factors associated with the genomic (e.g., chromosomal, mitochondrial, etc.) DNA, and identifying the one or more factors bound to the targeting moieties of the oligonucleotide paints.

In certain aspects, a plurality of oligonucleotide paints specific to a plurality of different chromosomal and/or mitochondrial DNA sequences are used. In other aspects, a plurality of oligonucleotide paints specific to a plurality of different chromosomal regions are used. In yet other aspects, the retrievable moieties are one component of binding pairs such as, for example, biotin-streptavidin. In other aspects, the oligonucleotide paints are retrieved by binding the retrievable moiety. In yet other aspects, the targeting moieties are inert until activation, e.g., by heat activation, light activation, chemical activation and any combination of these. In certain aspects, the targeting moieties bind a protein, a peptide, a carbohydrate, a lipid, a chemical moiety (e.g., a methyl group or an acetyl group or the like) or any combination of these. In still other aspects, the one or more factors include nucleic acid sequences (e.g., DNA and/or RNA), polypeptides (e.g., of one or more histone proteins, scaffold proteins, transcription factors, DNA binding proteins, DNA repair factors, nucleases and the like), carbohydrates, lipids, chemical moieties and the like and any combination of these. In certain aspects, the methods include the use of a set of oligonucleotide paints to identify factors associated with a plurality of sub-chromosomal regions, e.g., at least 50, 100, 1000 or more sub-chromosomal regions. In other aspects, the oligonucleotide paints bind genomic (e.g., chromosomal and/or mitochondrial) DNA present in a single copy, in low copy numbers, in moderately repetitive elements or in highly repetitive elements.

In other exemplary embodiments, methods for identifying one or more factors associated with genomic (e.g., chromosomal, mitochondrial, etc.) DNA are provided. The methods include the steps of providing a biological sample including genomic (e.g., chromosomal, mitochondrial, etc.) DNA, contacting the biological sample with a plurality of oligonucleotide paints, wherein the oligonucleotide paints include a targeting moiety, and wherein substantially all of the oligonucleotide paints have a unique nucleotide sequence relative to one another, allowing the oligonucleotide paints to bind the genomic (e.g., chromosomal, mitochondrial, etc.) DNA, allowing the targeting moieties to bind to the one or more factors associated with the genomic (e.g., chromosomal, mitochondrial, etc.) DNA, retrieving the oligonucleotide paints and one or more factors by binding the retrievable moieties, and identifying the one or more factors bound to the targeting moieties of the oligonucleotide paints.

In certain aspects, the retrievable moieties are one component of a binding pair such as, for example, biotin-streptavidin. In other aspects, the oligonucleotide paints are retrieved by binding the retrievable moieties. In yet other aspects, the targeting moieties are inert until activation, e.g., by heat activation, light activation, chemical activation and any combination of these. In certain aspects, the targeting moieties bind a protein, a peptide, a carbohydrate, a lipid, a chemical moiety (e.g., a methyl group or an acetyl group or the like) or any combination of these. In still other aspects, the one or more factors include nucleic acid sequences (e.g., DNA and/or RNA), polypeptides (e.g., of one or more histone proteins, scaffold proteins, transcription factors, DNA binding proteins, DNA repair factors, nucleases and the like), carbohydrates, lipids, chemical moieties and the like and any combination of these. In certain aspects, the methods include the use of a set of oligonucleotide paints to identify factors associated with a plurality of sub-chromosomal regions, e.g., at least 50, 100, 1000 or more sub-chromosomal regions. In other aspects, the oligonucleotide paints bind genomic (e.g., chromosomal, mitochondrial, etc.) DNA present in a single copy, in low copy numbers, in moderately repetitive elements or in highly repetitive elements.

Further features and advantages of certain embodiments of the present invention will become more fully apparent in the following description of the embodiments and drawings thereof, and from the claims.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION

Figure 1:
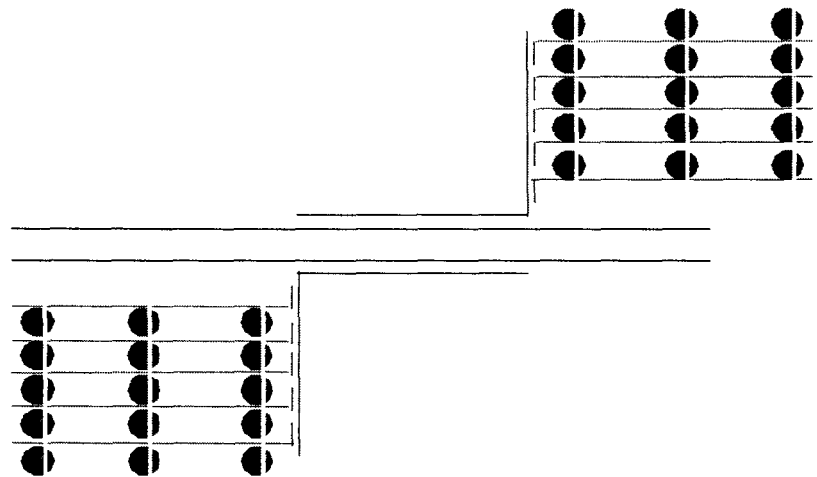
FIG. 1 schematically depicts a method for enhancing the recovery of targeted DNA fragments and their associated factors by combining branching and/or homing endonucleases according to an exemplary embodiment. The circles represent an epitope-tagged endonuclease that is a catalytically inactive mutant (e.g., HA-ISce1D218S) having a photo-activatable residue bound thereto. Alternatively, a wild-type homing endonuclease could be added in a buffer and/or using conditions that permit no activity (e.g., in situ hybridization buffer). The "L" shaped lines represent primary probe (e.g., PCR product). The lines bound to the circles represent secondary probe (amplifier that contains a homing endonuclease binding site). In certain aspects, photo-crosslinking is used to covalently link the homing endonuclease with nearby molecules. The tagged homing endonuclease is immunoprecipitated, capturing cross-linked proteins and nucleic acids. This strategy could provide a molecular ruler (for revealing the distance between various factors and/or between factors and DNA) by varying the overhang length of the 1° probe, the length of the 2° probe, and/or the spacing of the binding sites.

The principles of the present invention may be applied with particular advantage in methods of identifying and/or characterizing one or more factors that associate with, modify or otherwise interact with one or more oligonucleotide sequences of interest, e.g., chromosomal regions (e.g., sub-chromosomal regions) and/or one or more entire chromosomes. The methods described herein utilize oligonucleotide paints to capture factors associated with one or more oligonucleotide sequences of interest, e.g., chromosomal regions (e.g., sub-chromosomal regions) and/or one or more entire chromosomes.

As used herein, the terms "oligonucleotide paint" and "Oligopaint" refer to polynucleotides (e.g., DNA and/or RNA sequences) that have sequences complementary to an oligonucleotide sequence, e.g., a portion of a nucleic acid sequence, such as a DNA sequence (e.g., nuclear DNA, mitochondrial DNA, transfected DNA and the like) and/or an RNA sequence. In certain aspects, oligonucleotide paints and Oligopaints include one or more targeting moieties bound thereto. In other aspects, oligonucleotide paints and Oligopaints include one or more retrievable moieties bound thereto. In still other aspects, oligonucleotide paints and Oligopaints include both 1) one or more targeting moieties bound thereto, and 2) one or more retrievable moieties bound thereto. In yet other aspects, oligonucleotide paints and Oligopaints do not include detectable labels such as, e.g., fluors or other visually detectable labels. In still other aspects, oligonucleotide paints and Oligopaints do not include targeting moieties and/or retrievable moieties. According to certain aspects, a non-limiting example of oligonucleotide paints, Oligopaints and their methods of use are described in detail in U.S. Ser. No. 12/780,446, Filed May 14, 2010 (U.S. Publication No. 2010/0304994), and in the patent application corresponding to (U.S. Ser. No. 61/443,904, filed Feb. 17, 2011), each of which is incorporated herein by reference in its entirety for all purposes.

As used herein, the terms "bind" and "attach" refer to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

As used herein, the term "retrievable moiety" refers to a moiety that is present in or attached to a polynucleotide (e.g., an Oligopaint) that can be used to retrieve an oligonucleotide paint and, optionally, any factors bound to the oligonucleotide paint (e.g., one or more factors bound to a targeting moiety).

As used herein, the term "targeting moiety" refers to a moiety that is present in or attached to a polynucleotide (e.g., an Oligopaint) that can be used to specifically and/or non-specifically bind one or more factors that associate with, modify or otherwise interact with a nucleic acid sequence of interest (e.g., DNA (e.g., nuclear, mitochondrial, transfected and the like) and/or RNA), including, but not limited to, a protein, a peptide, a DNA sequence, an RNA sequence, a carbohydrate, a lipid, a chemical moiety or the like at or near the nucleotide sequence of interest to which one or more Oligopaints have hybridized. In certain aspects, factors that associate with a nucleic acid sequence of interest include, but are no limited to histone proteins (e.g., H1, H2A, H2B, H3, H4 and the like, including monomers and oligomers (e.g., dimers, tetramers, octamers and the like)) scaffold proteins, transcription factors, DNA binding proteins, DNA repair factors, DNA modification proteins (e.g., acetylases, methylases and the like).

In other aspects, factors that associate with, modify or otherwise interact with a nucleic acid sequence of interest are proteins including, but not limited to, proteins that are involved with gene regulation such as, e.g., proteins associated with chromatin (See, e.g., Dejardin and Kingston (2009) *Cell* 136:175), proteins that regulate (upregulate or downregulate) methylation, proteins that regulate (upregulate or down-regulate) acetylation, proteins that regulate (upregulate or downregulate) histone acetylation, proteins that regulate (upregulate or downregulate) transcription, proteins that regulate (upregulate or downregulate) post-transcriptional regulation, proteins that regulate (upregulate or downregulate) RNA transport, proteins that regulate (upregulate or downregulate) mRNA degradation, proteins that regulate (upregulate or down-regulate) translation, proteins that regulate (upregulate or downregulate) post-translational modifications and the like.

In certain aspects, a targeting and/or retrievable moiety is activatable. As used herein, the term "activatable" refers to a targeting and/or retrievable moiety that is inert (i.e., does not bind a target) until activated (e.g., by exposure of the activatable, targeting and/or retrievable moiety to light, heat, one or more chemical compounds or the like). In other aspects, a targeting and/or retrievable moiety can bind one or more targets without the need for activation of the targeting and/or retrievable moiety. Exemplary methods for attaching proteins, lipids, carbohydrates, nucleic acids and the like are described in Example VI infra. In certain aspects, a targeting moiety can be a non-targeting moiety that is cross-linked or otherwise modified to bind one or more factors that associate with, modify or otherwise interact with a nucleic acid sequence.

In certain exemplary embodiments, a targeting moiety, a retrievable moiety and/or polynucleotide (e.g., an Oligopaint) has a detectable label bound thereto. As used herein, the term "detectable label" refers to a label that can be used to identify a target (e.g., a factor associated with a nucleic acid sequence of interest, a chromosome or a sub-chromosomal region). Typically, a detectable label is attached to the 3'- or 5'-end of a polynucleotide (e.g., an Oligopaint). Alternatively, a detectable label is attached to an internal portion of an oligonucleotide (i.e., not at the 3' or the 5' end). Detectable labels may vary widely in size and compositions; the following references provide guidance for selecting oligonucleotide tags appropriate for particular embodiments: Brenner, U.S. Pat. No. 5,635,400; Brenner et al., *Proc. Natl. Acad. Sci.,* 97: 1665; Shoemaker et al. (1996) *Nature Genetics,* 14:450; Morris et al., EP Patent Pub. 0799897A1; Wallace, U.S. Pat. No. 5,981,179; and the like.

Methods for incorporating detectable labels into nucleic acid probes are well known. Typically, detectable labels (e.g., as hapten- or fluorochrome-conjugated deoxyribo-nucleotides) are incorporated into an oligopaint during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

In certain aspects, a suitable targeting moiety, retrievable moiety or detectable label includes, but is not limited to, a capture moiety such as a hydrophobic compound, an oligonucleotide, an antibody or fragment of an antibody, a protein, a peptide, a chemical cross-linker, an intercalator, a molecular cage (e.g., within a cage or other structure, e.g., protein cages, fullerene cages, zeolite cages, photon cages, and the like), or one or more elements of a capture pair, e.g., biotin-avidin, biotin-streptavidin, NHS-ester and the like, a thioether linkage, static charge interactions, van der Waals forces and the like (See, e.g., Holtke et al., U.S. Pat. Nos. 5,344,757; 5,702,888; and 5,354,657; Huber et al., U.S. Pat. No. 5,198,537; Miyoshi, U.S. Pat. No. 4,849,336; and Gait, PCT publication WO 91/17160). In certain aspects, a suitable targeting label, retrievable label or detectable label is an enzyme (e.g., a methylase and/or a cleaving enzyme). In one aspect, an antibody specific against the enzyme can be used to retrieve or detect the enzyme and accordingly, retrieve or detect an oligonucleotide sequence or factor attached to the enzyme. In another aspect, an antibody specific against the enzyme can be used to retrieve or detect the enzyme and, after stringent washes, retrieve or detect a factor or first oligonucleotide sequence that is hybridized to a second oligonucleotide sequence having the enzyme attached thereto.

Biotin, or a derivative thereof, may be used as an oligonucleotide (e.g., Oligopaint) label (e.g., as a targeting moiety, retrievable moiety and/or a detectable label), and subsequently bound by a avidin/streptavidin derivative (e.g., detectably labelled, e.g., phycoerythrin-conjugated streptavidin), or an anti-biotin antibody (e.g., a detectably labelled antibody). Digoxigenin may be incorporated as a label and subsequently bound by a detectably labelled anti-digoxigenin antibody (e.g., a detectably labelled antibody, e.g., fluoresceinated anti-digoxigenin). An aminoallyl-dUTP residue may be incorporated into an oligonucleotide and subsequently coupled to an N-hydroxy succinimide (NHS) derivatized fluorescent dye, such as those listed infra. In general, any member of a conjugate pair may be incorporated into a retrievable moiety and/or a detectable label provided that a detectably labelled conjugate partner can be bound to permit detection. As used herein, the term antibody refers to an antibody molecule of any class, or any sub-fragment thereof, such as an Fab.

Other suitable labels (targeting moieties, retrievable moieties and/or detectable labels) include, but are not limited to, fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for reaction, retrieval and/or detection: biotin/α-biotin, digoxigenin/a-digoxigenin, dinitrophenol (DNP)/α-DNP, 5-Carboxyfluorescein (FAM)/α-FAM.

Additional suitable labels (targeting moieties, retrievable moieties and/or detectable labels) include, but are not limited to, chemical cross-linking agents. Cross-linking agents typically contain at least two reactive groups that are reactive towards numerous groups, including, but not limited to, sulfhydryls and amines, and create chemical covalent bonds between two or more molecules. Functional groups that can be targeted with cross-linking agents include, but are not limited to, primary amines, carboxyls, sulfhydryls, carbohydrates and carboxylic acids. Protein molecules have many of these functional groups and therefore proteins and peptides can be readily conjugated using cross-linking agents. Cross-linking agents are well known in the art and are commercially available (Thermo Scientific (Rockford, Ill.)).

Fluorescent labels and their attachment to oligonucleotides (e.g., to targeting moieties, retrievable moieties and/or detectable labels) are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); Wetmur, *Critical Reviews in Biochemistry and Molecular Biology*, 26:227-259 (1991); and the like. Particular methodologies applicable to the Oligopaint methods and compositions described herein are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one embodiment, one or more fluorescent dyes are used as labels for Oligopaints, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Amines can be incorporated into Oligopaints, and labels can be added via the amines using methods known in the art. As used herein, the term "fluorescent label" includes a signaling moiety that conveys information through the fluorescent absorption and/or emission properties of one or more molecules. Such fluorescent properties include fluorescence intensity, fluorescence life time, emission spectrum characteristics, energy transfer and the like.

Commercially available fluorescent nucleotide analogues readily incorporated into the Oligopaints include, for example, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY TM 630/650-14-dUTP, BODIPY TM 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY TM FL-14-UTP, BODIPY TMR-14-UTP, BODIPY TM TR-14-UTP, RHODAMINE GREEN™-5-UTP, ALEXA FLUOR™ 488-5-UTP, ALEXA FLUOR™ 546-14-UTP (Molecular Probes, Inc. Eugene, Oreg.). Protocols are available for custom synthesis of nucleotides having other fluorophores. Henegariu et al., "Custom Fluorescent-Nucleotide Synthesis as an Alternative Method for Nucleic Acid Labeling," *Nature Biotechnol.* 18:345-348 (2000).

Other fluorophores available for post-synthetic attachment include, inter alia, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like) (available from Thermo Fisher Scientific, Rockford, Ill.), Texas Red (available from Molecular Probes, Inc., Eugene, Oreg.), and Cy2, Cy3.5, Cy5.5, and Cy7 (available from Amersham Biosciences, Piscataway, N.J. USA, and others).

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Metallic silver particles may be coated onto the surface of the array to enhance signal from fluorescently labelled oligonucleotide sequences bound to an array. Lakowicz et al. (2003) *BioTechniques* 34:62.

Detection method(s) used will depend on the particular detectable labels used in the reactive labels, retrievable labels and/or detectable labels. In certain exemplary embodiments, chromosomes and/or chromosomal regions having one or more reactive labels, retrievable labels detectable labels and/or Oligopaints bound thereto may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

In certain aspects, an oligonucleotide paint or an Oligopaint contains sequences complementary to an oligonucleotide sequence of a particular chromosome or sub-chromosomal region of a particular chromosome. Probes and Oligopaints can be generated from synthetic probes and arrays that are, optionally, computationally patterned (rather than using natural DNA sequences and/or chromosomes as a template). Oligopaints can be used to hybridize to a target nucleic acid sequence of interest, e.g., chromosomes and sub-chromosomal regions of chromosomes during various phases of the cell cycle including, but not limited to, interphase, preprophase, prophase, prometaphase, metaphase, anaphase, telophase and cytokenesis.

In certain exemplary embodiments, oligonucleotide paints or Oligopaints are complementary to genomic nucleic sequences that are present in low or single copy numbers (e.g., genomic nucleic sequences that are not repetitive elements). As used herein, the term "repetitive element" refers to a DNA sequence that is present in many identical or similar copies in the genome. Repetitive elements are not intended to refer to a DNA sequence that is present on each copy of the same chromosome (e.g., a DNA sequence that is present only once, but is found on both copies of chromosome 11, would not be considered a repetitive element, and would be considered a sequence that is present in the genome as one copy). The genome consists of three broad sequence components: Single copy or at least very low copy number DNA (approximately 60% of the human genome); moderately repetitive elements (approximately 30% of the human genome); and highly repetitive elements (approximately 10% of the human genome). For a review, see Human Molecular Genetics, Chapter 7 (1999), John Wiley & Sons, Inc.

As used herein, the term "chromosome" refers to the support for the genes carrying heredity in a living cell, including DNA, protein, RNA and other associated factors. The conventional international system for identifying and numbering the chromosomes of the human genome is used herein. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, *Homo, Drosophila, Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum* and the like.

When fluorescently labelled targeting moieties, retrievable moieties, detectable labels and/or Oligopaints are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labelled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

The in situ hybridization methods described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

In certain exemplary embodiments, Oligopaints include multiple chromosome-specific probes, which are differentially labelled (i.e., at least two of the chromosome-specific probes are differently labelled). Various approaches to multi-color chromosome painting have been described in the art and can be adapted to the present invention following the guidance provided herein. Examples of such differential labeling ("multicolor FISH") include those described by Schrock et al. (1996) *Science* 273:494, and Speicher et al. (1996) *Nature Genet.* 12:368). Schrock et al. describes a spectral imaging method, in which epifluorescence filter sets and computer software is used to detect and discriminate between multiple differently labelled DNA probes hybridized simultaneously to a target chromosome set. Speicher et al. describes using different combinations of 5 fluorochromes to label each of the human chromosomes (or chromosome arms) in a 27-color FISH termed "combinatorial multifluor FISH"). Other suitable methods may also be used (see, e.g., Ried et al., 1992, *Proc. Natl. Acad. Sci. USA* 89:1388-92).

Hybridization of the Oligopaints of the invention to target chromosomes sequences can be accomplished by standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized oligonucleotides (e.g., hybridized Oligopaints). The reagents used in each of these steps and their conditions of use vary depending on the particular situation. For instance, step 3 will not always be necessary as the Oligopaints described herein can be designed to avoid repetitive sequences). Hybridization conditions are also described in U.S. Pat. No. 5,447,841. It will be appreciated that numerous variations of in situ hybridization protocols and conditions are known and may be used in conjunction with the present invention by practitioners following the guidance provided herein.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual*, 2nd Ed. Cold Spring Harbor Press (1989) and Anderson *Nucleic Acid Hybridization*, 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

In certain exemplary embodiments, synthesis of oligonucleotides (e.g., Oligopaints) and/or amplification of oligonucleotides (e.g., Oligopaints) can be performed using a support. In certain aspects, multiple supports (tens, hundreds, thousands or more) may be utilized (e.g., synthesized, amplified, hybridized or the like) in parallel. Suitable supports include, but are not limited to, slides (e.g., microscope slides), beads, chips, particles, strands, gels, sheets, tubing (e.g., microfuge tubes, test tubes, cuvettes), spheres, containers, capillaries, microfibers, pads, slices, films, plates (e.g., multi-well plates), microfluidic supports (e.g., microarray chips, flow channel plates, biochips and the like) and the like. In various embodiments, the solid supports may be biological, nonbiological, organic, inorganic or combinations thereof. When using supports that are substantially planar, the support may be physically separated into regions, for example, with trenches, grooves, wells, or chemical barriers (e.g., lacking a lipid-binding coating). In exemplary embodiments, supports can be made of a variety of materials including, but not limited to glass, quartz, ceramic, plastic, polystyrene, methylstyrene, acrylic polymers, titanium, latex, sepharose, cellulose, nylon and the like and any combination thereof. Such supports and their uses are well known in the art.

In certain exemplary embodiments, supports may have functional groups on their surface which can be used to attach a lipid bilayer (e.g., a phospholipid bilayer) to the support. For example, at least a portion of the support can be coated with silane and dextran (e.g., high molecular weight dextran). Dextran in its hydrated form can function as a molecular cushion for the membrane and is capable of binding lipids on the support. Suitable functional groups include, but are not limited to, silicon oxides (e.g., $SiO_2$), $MgF_2$, $CaF_2$, mica, polyacrylamide, dextran and the like and any combination thereof.

In certain exemplary embodiments, methods of generating and amplifying synthetic oligonucleotide sequences, e.g., Oligopaint sequences, are provided. As used herein, the term "oligonucleotide" is intended to include, but is not limited to, a single-stranded DNA or RNA molecule, typically prepared by synthetic means. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, *Biochemistry*, Third Ed. (1988), incorporated herein by reference in its entirety for all purposes). As used herein, the term "polynucleotide" is intended to include, but is not limited to, two or more oligonucleotides joined together (e.g., by hybridization, ligation, polymerization and the like).

The term "operably linked," when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

In certain exemplary embodiments, nucleotide analogs or derivatives will be used, such as nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer. The nucleotides can have a protecting group which is linked to, and masks, a reactive group on the nucleotide. A variety of protecting groups are useful in the invention and can be selected depending on the synthesis techniques employed and are discussed further below. After the nucleotide is attached to the support or growing nucleic acid, the protecting group can be removed.

Oligonucleotides or fragments thereof may be purchased from commercial sources. Oligonucleotide sequences may be prepared by any suitable method, e.g., the phosphoramidite method described by Beaucage and Carruthers ((1981) *Tetrahedron Lett.* 22: 1859) or the triester method according to Matteucci et al. (1981) *J. Am. Chem. Soc.* 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides and chips containing oligonucleotides may also be obtained commercially from a variety of vendors.

In an exemplary embodiment, oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single stranded DNA molecule of desired sequence. An exemplary type of instrument is the type shown in FIG. 5 of U.S. Pat. No. 6,375,903, based on the use of reflective optics. It is a desirable that this type of maskless array synthesizer is under software control. Since the entire process of microarray synthesis can be accomplished in only a few hours, and since suitable software permits the desired DNA sequences to be altered at will, this class of device makes it possible to fabricate microarrays including DNA segments of different sequence every day or even multiple times per day on one instrument. The differences in DNA sequence of the DNA segments in the microarray can also be slight or dramatic, it makes no difference to the process. The MAS instrument may be used in the form it would normally be used to make microarrays for hybridization experiments, but it may also be adapted to have features specifically adapted for the compositions, methods, and systems described herein. For example, it may be desirable to substitute a coherent light source, i.e., a laser, for the light source shown in FIG. 5 of the above-mentioned U.S. Pat. No. 6,375,903. If a laser is used as the light source, a beam expanded and scatter plate may be used after the laser to transform the narrow light beam from the laser into a broader light source to illuminate the micromirror arrays used in the maskless array synthesizer. It is also envisioned that changes may be made to the flow cell in which the microarray is synthesized. In particular, it is envisioned that the flow cell can be compartmentalized, with linear rows of array elements being in fluid communication with each other by a common fluid channel, but each channel being separated from adjacent channels associated with neighboring rows of array elements. During microarray synthesis, the channels all receive the same fluids at the same time. After the DNA segments are separated from the substrate, the channels serve to permit the DNA segments from the row of array elements to congregate with each other and begin to self-assemble by hybridization.

Other methods for synthesizing oligonucleotides (e.g., Oligopaints) include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in U.S. Pat. No. 5,384,261.

Additional methods applicable to synthesis and/or amplification of oligonucleotides (e.g., Oligopaints) on a single support are described, for example, in U.S. Pat. No. 5,384,261. For example reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink-jet printer. In other embodiments, the dispenser includes a series of tubes, a manifold, an array of pipettes, or the like so that various reagents can be delivered to the reaction regions simultaneously.

Pin-based methods for synthesis of oligonucleotides on a solid support are described, for example, in U.S. Pat. No.

5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In yet another embodiment, a plurality of oligonucleotides (e.g., Oligopaints) may be synthesized on multiple supports. One example is a bead based synthesis method which is described, for example, in U.S. Pat. Nos. 5,770,358, 5,639,603, and 5,541,061. For the synthesis of molecules such as oligonucleotides on beads, a large plurality of beads are suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

In certain embodiments, a plurality of oligonucleotides (e.g., Oligopaints) may be synthesized, amplified and/or used in conjunction with beads and/or bead-based arrays. As used herein, the term "bead" refers to a discrete particle that may be spherical (e.g., microspheres) or have an irregular shape. Beads may be as small as approximately 0.1 µm in diameter or as large approximately several millimeters in diameter. Beads typically range in size from approximately 0.1 µm to 200 µm in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In certain aspects, beads may have functional groups on their surface which can be used to oligonucleotides (e.g., Oligopaints) to the bead. Oligonucleotide sequences can be attached to a bead by hybridization (e.g., binding to a polymer), covalent attachment, magnetic attachment, affinity attachment and the like. For example, the bead can be coated with streptavidin and the nucleic acid sequence can include a biotin moiety. The biotin is capable of binding streptavidin on the bead, thus attaching the nucleic acid sequence to the bead. Beads coated with streptavidin, oligo-dT, and histidine tag binding substrate are commercially available (Dynal Biotech, Brown Deer, Wis.). Beads may also be functionalized using, for example, solid-phase chemistries known in the art, such as those for generating nucleic acid arrays, such as carboxyl, amino, and hydroxyl groups, or functionalized silicon compounds (see, for example, U.S. Pat. No. 5,919,523).

Various exemplary protecting groups useful for synthesis of oligonucleotides on a solid support are described in, for example, Atherton et al., 1989, Solid Phase Peptide Synthesis, IRL Press. In various embodiments, the methods described herein utilize solid supports for immobilization of nucleic acids. For example, oligonucleotides may be synthesized on one or more solid supports. Exemplary solid supports include, for example, slides, beads, chips, particles, strands, gels, sheets, tubing, spheres, containers, capillaries, pads, slices, films, or plates. In various embodiments, the solid supports may be biological, nonbiological, organic, inorganic, or combinations thereof. When using supports that are substantially planar, the support may be physically separated into regions, for example, with trenches, grooves, wells, or chemical barriers (e.g., hydrophobic coatings, etc.). Supports that are transparent to light are useful when the assay involves optical detection (see e.g., U.S. Pat. No. 5,545,531). The surface of the solid support will typically contain reactive groups, such as carboxyl, amino, and hydroxyl or may be coated with functionalized silicon compounds (see e.g., U.S. Pat. No. 5,919,523).

In one embodiment, the oligonucleotides synthesized on the solid support may be used as a template for the production of Oligopaints. For example, the support bound oligonucleotides may be contacted with primers that hybridize to the oligonucleotides under conditions that permit chain extension of the primers. The support bound duplexes may then be denatured, pooled and subjected to further rounds of amplification to produce Oligopaints in solution. In another embodiment, the support-bound oligonucleotides may be removed from the solid, pooled and amplified to produce Oligopaints in solution. The oligonucleotides may be removed from the solid support, for example, by exposure to conditions such as acid, base, oxidation, reduction, heat, light, metal ion catalysis, displacement or elimination chemistry, or by enzymatic cleavage.

In one embodiment, oligonucleotides may be attached to a solid support through a cleavable linkage moiety. For example, the solid support may be functionalized to provide cleavable linkers for covalent attachment to the oligonucleotides. The linker moiety may be one, two, three, four, five, six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., Ann. Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. The linker may be cleaved using two approaches, either (a) simultaneously under the same conditions as the deprotection step or (b) subsequently utilizing a different condition or reagent for linker cleavage after the completion of the deprotection step.

The covalent immobilization site may either be at the 5' end of the oligonucleotide or at the 3' end of the oligonucleotide. In some instances, the immobilization site may be within the oligonucleotide (i.e. at a site other than the 5' or 3' end of the oligonucleotide). The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al, Nucleic Acids Research 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al. J. of Org. Chem. 61:525-529 (1996), Kahl et al., J. of Org. Chem. 64:507-510 (1999), Kahl et al., J. of Org. Chem. 63:4870-4871 (1998), Greenberg et al., J. of Org. Chem. 59:746-753 (1994), Holmes et al., J. of Org. Chem. 62:2370-2380 (1997), and U.S. Pat. No. 5,739,386. Ortho-nitobenzyl-based linkers, such as hydroxymethyl, hydroxyethyl, and Fmoc-aminoethyl carboxylic acid linkers, may also be obtained commercially.

In another embodiment, oligonucleotides may be removed from a solid support by an enzyme such as a nuclease. For example, oligonucleotides may be removed from a solid support upon exposure to one or more restriction endonucleases, including, for example, class IIs restriction enzymes. A restriction endonuclease recognition sequence may be incorporated into the immobilized oligonucleotides and the oligonucleotides may be contacted with one or more restriction endonucleases to remove the oligonucleotides from the support. In various embodiments, when using enzymatic cleavage to remove the oligonucleotides from the support, it may be desirable to contact the single stranded immobilized oligonucleotides with primers, polymerase and dNTPs to form immobilized duplexes. The duplexes may then be contacted with the enzyme (e.g., a restriction endonuclease) to remove the duplexes from the surface of the support. Methods for synthesizing a second strand on a support bound oligonucleotide and methods for enzymatic removal of support bound duplexes are described, for example, in U.S. Pat. No. 6,326,489. Alternatively, short oligonucleotides that are complementary to the restriction endonuclease recognition and/or cleavage site (e.g., but are not complementary to the entire support bound oligonucleotide) may be added to the support bound oligonucleotides under hybridization conditions to facilitate cleavage by a restriction endonuclease (see e.g., PCT Publication No. WO 04/024886).

In yet another embodiment, a plurality of oligonucleotides (e.g., Oligopaints) may be synthesized and/or amplified in solution. Methods of synthesizing oligonucleotide sequences are well-known in the art (See, e.g., Seliger (1993) *Protocols for Oligonucleotides and Analogs: Synthesis and Properties*, vol. 20, pp. 391-435, Efimov (2007) *Nucleosides, Nucleotides & Nucleic Acids* 26:8, McMinn et al. (1997) *J. Org. Chem.* 62:7074, Froehler et al. (1986) *Nucleic Acids Res.* 14:5399, Garegg (1986) *Tet. Lett.* 27:4051, Efimov (1983) *Nucleic Acids Res.* 11:8369, Reese (1978) *Tetrahedron* 34:3143).

In certain embodiments, oligonucleotides (e.g., Oligopaints) are double stranded (ds). In certain aspects, a ds oligonucleotide may be synthesized as two single stranded oligonucleotides that are hybridized together, thus forming a ds oligonucleotide. Alternatively, a ds oligonucleotide may be synthesized is a ds form (e.g., using a ss oligonucleotide as a template). In other embodiments, oligonucleotides (e.g., Oligopaints) are single stranded (ss). In certain aspects, a ss oligonucleotide is generated in a ss form. In other aspects, a ss oligonucleotide is synthesized in a ds form and is converted to ss form subsequent to synthesis using any of a variety of methods well known in the art (e.g., by incorporating dUs into the ds oligonucleotide during synthesis that can be cleaved after synthesis, by chemical cleavage after synthesis, by enzymatic cleavage after synthesis, by nuclease digestion after synthesis, by light based cleavage after synthesis and the like).

Exemplary chemically cleavable internucleotide linkages for use in the methods described herein include, for example, β-cyano ether, 5'-deoxy-5'-aminocarbamate, 3' deoxy-3'-aminocarbamate, urea, 2'cyano-3',5'-phosphodiester, 3'-(S)-phosphorothioate, 5'-(S)-phosphorothioate, 3'-(N)-phosphoramidate, 5'-(N)-phosphoramidate, α-amino amide, vicinal diol, ribonucleoside insertion, 2'-amino-3',5'-phosphodiester, allylic sulfoxide, ester, silyl ether, dithioacetal, 5'-thio-furmal, α-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include β-cyano ether, 5'-deoxy-5'-aminocarbamate, 3'-deoxy-3'-aminocarbamate, urea, 2'-cyano-3',5'-phosphodiester, 2'-amino-3', 5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Enzymatic cleavage may be mediated by including a restriction endonuclease cleavage site in the oligonucleotide sequence. After synthesis of a ds oligonucleotide, the ds oligonucleotide may be contacted with one or more endonucleases to remove one strand. A wide variety of restriction endonucleases having specific binding and/or cleavage sites are commercially available, for example, from New England Biolabs (Ipswich, Mass.).

In various embodiments, the methods disclosed herein comprise amplification of oligonucleotide sequences including, for example, Oligopaints. Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, universal primers will be used to amplify nucleic acid sequences such as, for example, Oligopaints. The term "universal primers" refers to a set of primers (e.g., a forward and reverse primer) that may be used for chain extension/amplification of a plurality of polynucleotides, e.g., the primers hybridize to sites that are common to a plurality of polynucleotides. For example, universal primers may be used for amplification of all, or essentially all, polynucleotides in a single pool. In certain aspects, forward primers and reverse primers have the same sequence. In other aspects, the sequence of forward primers differs from the sequence of reverse primers. In still other aspects, a plurality of universal primers are provided, e.g., tens, hundreds, thousands or more.

In certain embodiments, the universal primers may be temporary primers that may be removed after amplification via enzymatic or chemical cleavage. In certain embodiments, the universal primers may be temporary primers that may be removed after amplification via enzymatic or chemical cleavage. In other embodiments, the universal primers may comprise a modification that becomes incorporated into the polynucleotide molecules upon chain extension. Exemplary modifications include, for example, a 3' or 5' end cap, a label (e.g., fluorescein), or a tag (e.g., a tag that facilitates immobilization or isolation of the polynucleotide, such as, biotin, etc.).

In exemplary embodiments, primers may be designed to be temporary to permit removal of the primers. Temporary primers may be designed so as to be removable by chemical, thermal, light based, or enzymatic cleavage. Cleavage may occur upon addition of an external factor (e.g., an enzyme, chemical, heat, light, etc.) or may occur automatically after a certain time period (e.g., after n rounds of amplification). In one embodiment, temporary primers may be removed by chemical cleavage. For example, primers having acid labile or base labile sites may be used for amplification. The amplified pool may then be exposed to acid or base to remove the primer at the desired location. Alternatively, the temporary primers may be removed by exposure to heat and/or light. For example, primers having heat labile or photolabile sites may be used for amplification. The amplified pool may then be exposed to heat and/or light to remove the primer/primer binding sites at the desired location. In another embodiment, an RNA primer may be used for amplification thereby forming short stretches of RNA/DNA hybrids at the ends of the nucleic acid molecule. The primer site may then be removed by exposure to an RNase (e.g., RNase H). In various embodiments, the method for removing the primer may only cleave a single strand of the amplified duplex thereby leaving 3' or 5' overhangs. Such overhangs may be removed using an exonuclease to form blunt ended double stranded duplexes. For example, $RecJ_f$ may be used to remove single stranded 5' overhangs and Exonuclease I or Exonuclease T may be used to remove single stranded 3' overhangs. Additionally, $S_1$ nuclease, $P_1$ nuclease, mung bean nuclease, and CEL I nuclease, may be used to remove single stranded regions from a nucleic acid molecule. $RecJ_f$, Exonuclease I, Exonuclease T, and mung bean nuclease are commercially available, for example, from New England Biolabs (Ipswich, Mass.). S1 nuclease, P1 nuclease and CEL I nuclease are described, for example, in Vogt, V. M., *Eur. J. Biochem.*, 33: 192-200 (1973); Fujimoto et al., *Agric. Biol. Chem.* 38: 777-783 (1974); Vogt, V. M., *Methods Enzymol.* 65: 248-255 (1980); and Yang et al., *Biochemistry* 39: 3533-3541 (2000).

In one embodiment, the temporary primers may be removed from a nucleic acid by chemical, thermal, or light based cleavage as described supra. In other embodiments, primers may be removed using enzymatic cleavage. For example, primers may be designed to include a restriction endonuclease cleavage site. After amplification, the pool of nucleic acids may be contacted with one or more endonucleases to produce double stranded breaks thereby removing the primers. In certain embodiments, the forward and reverse primers may be removed by the same or different restriction endonucleases. Any type of restriction endonuclease may be used to remove the primers/primer binding sites from nucleic acid sequences. In various embodiments, restriction endonucleases that produce 3' overhangs, 5' overhangs or blunt ends may be used.

In certain embodiments, it may be desirable to utilize a primer comprising one or more modifications such as a cap (e.g., to prevent exonuclease cleavage), a linking moiety (such as those described above to facilitate immobilization of an oligonucleotide onto a substrate), or a label (e.g., to facilitate detection, isolation and/or immobilization of a nucleic acid construct). Suitable modifications include, for example, various enzymes, prosthetic groups, luminescent markers, bioluminescent markers, fluorescent markers (e.g., fluorescein), radiolabels (e.g., $^{32}$P, $^{35}$S, etc.), biotin, polypeptide epitopes, etc. as described further herein.

Embodiments of the present invention are directed to oligonucleotide sequences (e.g., Oligopaints) having one or more amplification sequences or amplification sites. As used herein, the term "amplification site" is intended to include, but is not limited to, a nucleic acid sequence located at the 5' and/or 3' end of the oligonucleotide sequences of the present invention which hybridizes a complementary nucleic acid sequence. In one aspect of the invention, an amplification site is removed from the oligonucleotide after amplification. In another aspect of the invention, an amplification site includes one or more restriction endonuclease recognition sequences recognized by one or more restriction enzymes. In another aspect, an amplification site is heat labile and/or photo labile and is cleavable by heat or light, respectively. In yet another aspect, an amplification site is a ribonucleic acid sequence cleavable by RNase. In still another aspect, an amplification site is chemically cleavable (e.g., using acid and/or base).

As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distances from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Ipswich, Mass.). Information about the recognition sites, cut sites and conditions for digestion using type IIs endonucleases may be found, for example, on the Worldwide Web at neb.com/nebecomm/enzymefindersearch bytypeIIs.asp). Restriction endonuclease sequences and restriction enzymes are well known in the art and restriction enzymes are commercially available (New England Biolabs).

Certain exemplary embodiments are directed to the use of computer software to automate design and/or interpretation of genomic spacings, repeat-discriminating SNPs and/or colors for each specific oligopaint set. Such software may be used in conjunction with individuals performing interpretation by hand or in a semi-automated fashion or combined with an automated system. In at least some embodiments, the design and/or interpretation software is implemented in a program written in the JAVA programming language. The program may be compiled into an executable that may then be run from a command prompt in the WINDOWS XP operating system. Unless specifically set forth in the claims, the invention is not limited to implementation using a specific programming language, operating system environment or hardware platform.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure and accompanying claims.

EXAMPLE I

Overall Strategy for Identifying One or More Factors Associated with a Nucleic Acid Sequence of Interest 1. Synthesize Oligopaints having a retrievable moiety (and optional targeting moiety) bound thereto.
2. Provide a biological sample and prepare sample (e.g., prepare chromosomes) so that it will bind Oligopaints.
3. Incubate sample and Oligopaints together to allow hybridization of Oligopaint to nucleic acid sequence of interest and one or more factors associated with nucleic acid sequence of interest.
4. Retrieve one or more factors associated with nucleic acid sequence of interest.
5. Identify on or more factors associated with nucleic acid sequence of interest.

REFERENCES

Lowenstein et al. (2004) *Mol. Biol. Cell* 15:5678
Dejardin and Kingston (2009) *Cell* 136:175
Carter et al. (2002) *Nat. Genet.* 32:623

EXAMPLE II

Combining Branching and Homing Endonucleases

FIG. 1 depicts a method of combining branching and homing endonucleases. Cells are fixed with paraformaldehyde, and in situ hybridization (ISH) is performed with a mix of primary and secondary probes. Recombinant, photoactivatable, tagged mutant homing endonuclease is added. Alternatively, wild-type homing endonuclease is added in a buffer/conditions that do not permit the activity of the homing endonuclease (e.g., ISH buffer itself). Photo-cross-linking covalently links homing endonuclease with nearby molecules. The tagged homing endonuclease is immunoprecipitated, capturing cross-linked proteins and nucleic acids. In certain aspects, a molecular ruler is provided by varying primary probe 5' overhang length and secondary probe length and binding site spacing.

EXAMPLE III

Ligation of Short Probes

Figure 2:
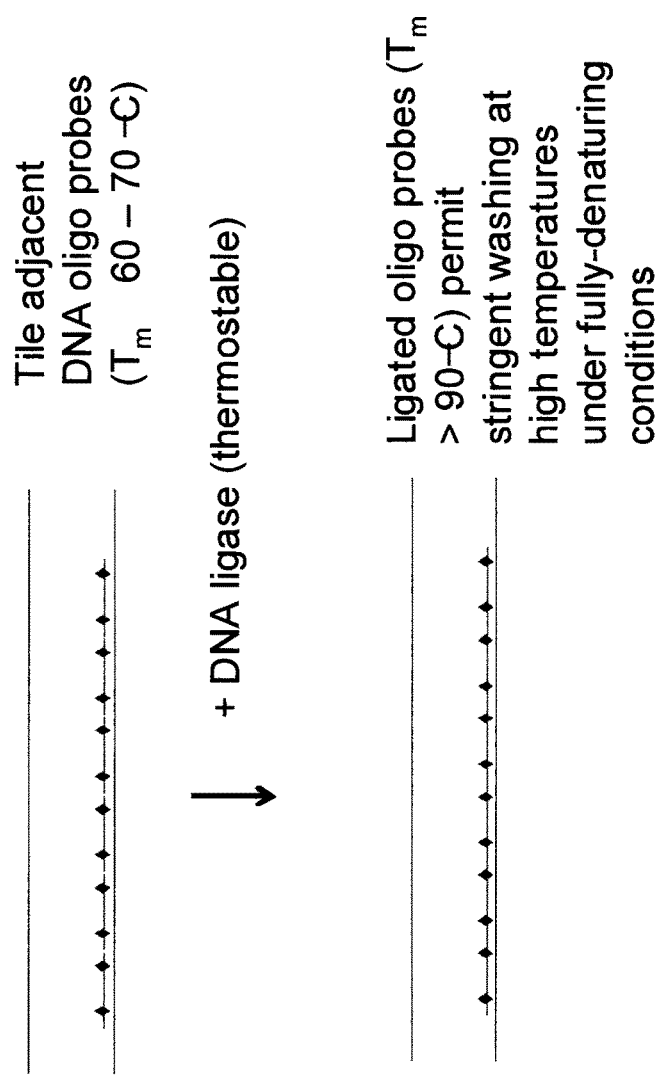
FIG. 2 schematically depicts a method for enhancing the hybridization of oligos to target DNA through the ligation of short probes according to an exemplary embodiment. The short lines associated with the diamonds are ssDNA oligonucleotide probes (e.g., 20-32 mers in size). The diamonds represent haptens (e.g., biotin or digoxigenin). The long lines represent genomic DNA. In certain aspects, this method is modified to accommodate chemical capture mechanisms (e.g. the addition of activatable residue(s) to the 3' end of every $2^{nd}$ or $3^{rd}$ oligo).

FIG. 2 depicts a method of ligating short probes to genomic DNA. Cells are fixed with paraformaldehyde, and ISH is performed with hapten-conjugated probes generated via PCR and enzymatic processing. The hybridization step is performed at high temperature (e.g. $T_m$ of short oligos −10° C.; room temperature hybridization would also likely be sufficient). Reaction is cooled to the working temp of a thermostable ligase (e.g. 37° C.; room temperature would also likely suffice). Ligation is allowed to occur. Unbound probe as well as oligos that have bound to sites without at least one adjacent oligo are removed via an extremely stringent wash at high T (approximately 80-85° C.). Probe-genomic DNA hybrids (and cross-linked proteins) are immunopurified via the probe-conjugated haptens. Key to approach: Only successfully ligated probes at sites of interest will be able to persist through the wash and be immunoprecipitated. In certain exemplary embodiments chemical capture mechanisms are incorporated, e.g., an activatable residue is added to the 3' end of every second or third oligo.

EXAMPLE IV

FISH and ChIPs

Figure 3:
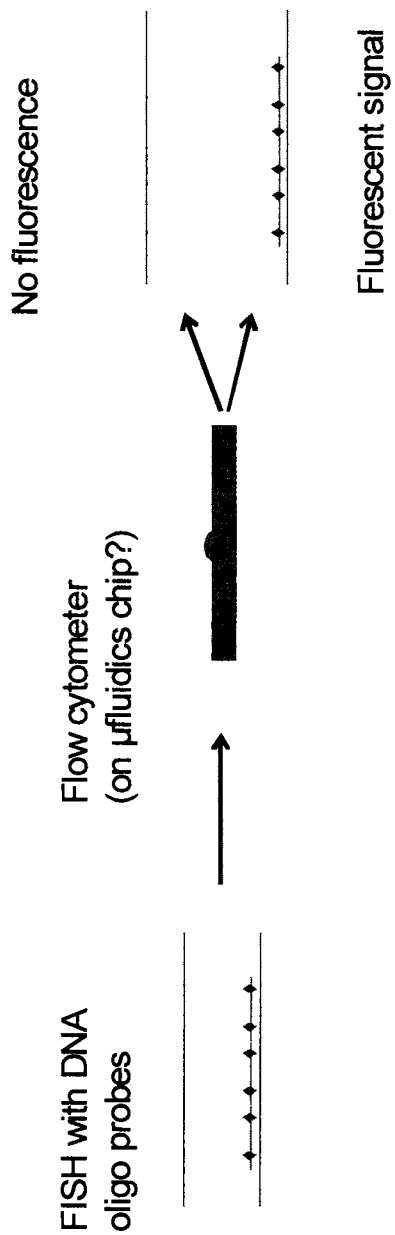
FIG. 3 schematically depicts a method to enhance the recovery of targeted DNA fragments and their associated factors. In certain embodiments, hybridization is performed using fluorophore- or hapten-conjugated DNA oligos such that, after hybridization, washes, and chromatin fragmentation by sonication or enzymatic digest, "chunks" of chromatin can be flow sorted by fluorescence or other methods (e.g., those that can detect the presence of oligos by virtue of their haptens), wherein those chunks of chromatin associated with oligos are sorted into a vessel away from chunks of chromatin with no oligos. Note, haptens and 2° antibodies can be used to increase the mean particle size, allowing for fragmentation to smaller sizes. The short lines associated with the diamonds are ssDNA oligonucleotide probes (e.g., 32-40 mers in size). The diamonds represent haptens and/or fluorophores. The long lines represent genomic DNA.

FIG. 3 schematically depicts ISH using hapten-conjugated probes. Cells are fixed with paraformaldehyde, and ISH is performed with hapten-conjugated probes generated via PCR and enzymatic processing. The hybridization step is performed using hapten- or fluorophore-conjugated DNA oligo probes. After hybridization and washes, chromatin is fragmented by sonication or enzymatic digest to create approximately 5 kb to 10 kb fragments. The fragments are flow sorted by their fluorescence such that fragments with oligos hybridized thereto will be sorted to a vessel away from fragments containing no oligos hybridized thereto. In certain aspects, haptens and secondary antibodies are used to increase mean particle size, allowing for fragmentation to smaller sizes.

EXAMPLE V

Methods for Washing ISH Samples

Figure 4:
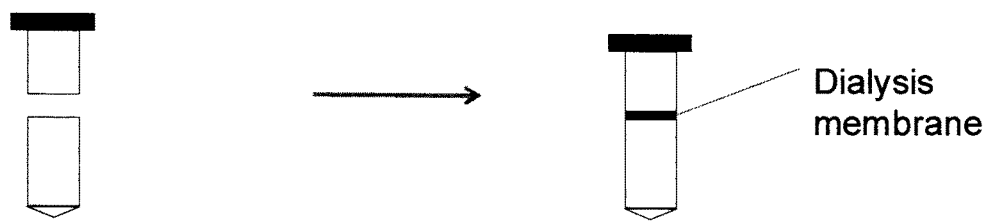
FIG. 4 schematically depicts a method of washing samples undergoing in situ hybridization (ISH) according an exemplary embodiment.

FIG. 4 schematically depicts one method for washing ISH samples. In certain aspects, a conical centrifuge tube with a separable body (e.g., screw off body) is used. The use of a centrifuge tube allows pelleting of cells undergoing ISH. The use of a separable body allows manipulation of a pellet (e.g., resuspension of the pellet), while use of dialysis membrane allows stringent washing (e.g., via diffusion, chemical and/or heat conditions) of unbound ISH probe without a need for fixing cells to an immobilized substrate such as a glass slide.

EXAMPLE VI

Attachment of Proteins, Lipids, Carbohydrates, Nucleic Acids and the Like to Oligonucleotide Sequences The following reactions are used to covalently attach proteins, lipids, carbohydrates or nucleic acid sequences to oligonucleotide sequences.

Protein Capture

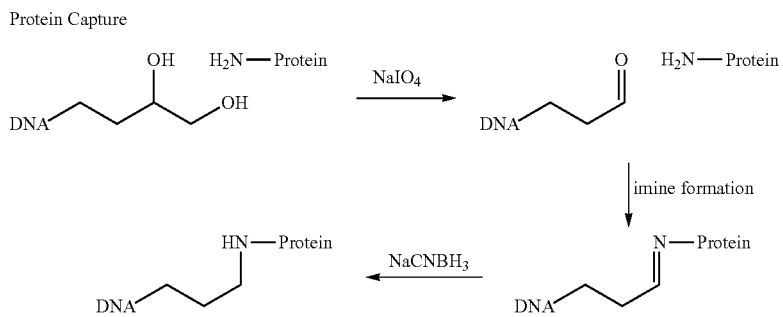

This strategy will also capture any RNA or sugar that is close to any protein that is covalently or even non-covalently attached to the oligo.

Unsaturated Lipid Capture

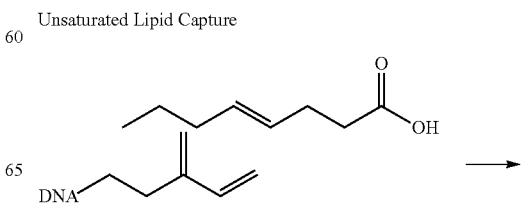

-continued

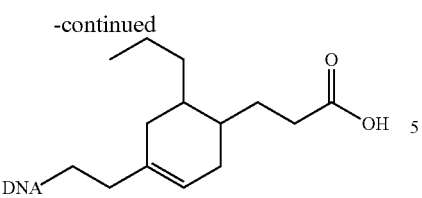

This strategy involves the Diels-Alder reaction.

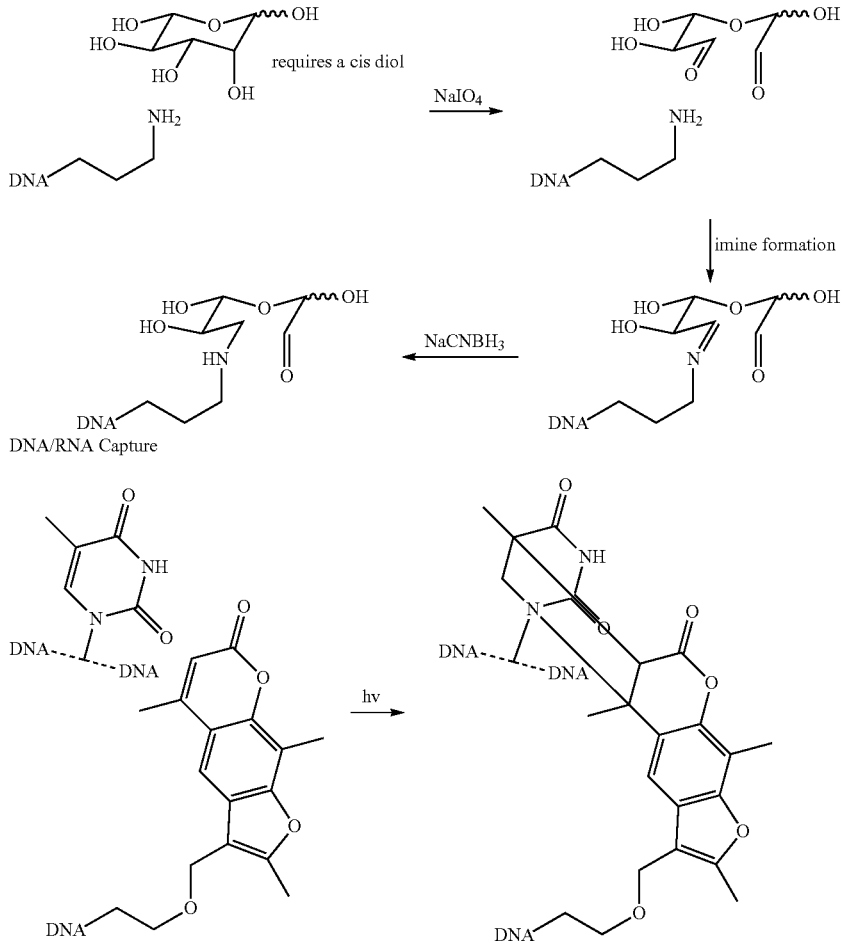

EXAMPLE VII

TRAP Variation

A hapten, such as digoxigenin, is attached to the oligo and the hapten is targeted with a reactive molecule, such as an anti-digoxigenin Fab fragment attached to horseradish peroxidase. Addition of biotin-tyramide to the sample then leads to covalent attachment of biotin to local factors via action of the horseradish peroxidase on the biotin-tyramide. Biotin-containing factors can then be isolated by virtue of their biotin tag.

In certain aspects, many different oligos are tiled along the chromosome. Tiling along the chromosome gives much higher precision then methods known in the art (e.g., Carter et al. (Supra), which targets probes to transcripts, not DNA), as transcripts can wander far from their origin.

EXAMPLE VIII

Materials and Methods

Each of the following references is incorporated in its entirety for all purposes. Methods for making catalytic I-SceI mutants are described in Gruen et al. (2002) *Nucl. Acids Res.* 30:e29. Methods for making HA tagged I-SceI are described in Anglana and Bacchetti (1999) *Nucl. Acids Res.* 27:4276. Methods for performing in vivo photo-cross-linking are described in Suchanek et al. (2005) *Nat. Methods* 2:261. Methods for sorting DNA by fluorescence using flow cytometry are described in Goodwin et al. (1993) *Nucl. Acids Res.* 21:803. Thermostable ligases such as, e.g., AMP-LIGASE® (EPICENTRE Biotechnologies, Madison, Wis.), are commercially available.

What is claimed is:

1. A method for identifying one or more factors bound to one or more targeting moieties of a plurality of oligonucleotide paints in a biological sample by in situ hybridization, comprising the steps of:

hybridizing the plurality of oligonucleotide paints to different chromosomal regions of a chromosome in the biological sample by in situ hybridization, thereby forming hybridized oligonucleotide paints, wherein each of the oligonucleotide paints comprises a 5' primer sequence, a nucleotide sequence capable of hybridizing to a specific region of the chromosome, 3' primer sequence, and one or more targeting moieties, and the nucleotide sequence capable of hybridizing to the specific region of the chromosome is located between the 5' primer sequence and the 3' primer sequence and is different in each of the oligonucleotide paints and the 5' primer sequence and the 3' primer sequence comprises either nucleotide sequences of a universal primer or nucleotide sequences fully complementary to the universal primer;

removing the oligonucleotide paints unbound to the different chromosomal regions of the chromosome from the hybridized oligonucleotide paints;

covalently attaching the targeting moieties of the hybridized oligonucleotide paints to the one or more factors in the biological sample; and identifying the one or more factors bound to the one or more targeting moieties of the plurality of oligonucleotide paints in the biological sample by identifying the factors attached to the targeting moieties of the hybridized oligonucleotide paints.

2. The method of claim 1, wherein the one or more factors are selected from the group consisting of a protein, a peptide, a carbohydrate, a lipid, a chemical moiety and any combination thereof.

3. The method of claim 1, wherein the oligonucleotide paints are between about 20 base pairs and about 32 base pairs in length.

4. The method of claim 1, wherein the nucleotide sequence capable of hybridizing to the specific region of the chromosome is between about 32 base pairs and about 40 base pairs in length.

5. The method of claim 1, further comprising the step of retrieving the hybridized oligonucleotide paints after the attaching step, wherein the oligonucleotide paints further include a retrievable moiety.

6. The method of claim 5, wherein the retrievable moiety is one component of a binding pair.

7. The method of claim 5, wherein the retrievable moiety is biotin.

8. The method of claim 5, wherein the hybridized oligonucleotide paints are retrieved by binding the retrievable moiety.

9. The method of claim 1, further comprising activation of the targeting moieties of the hybridized oligonucleotide paints before the attaching step.

10. The method of claim 9, wherein the activation of the targeting moieties of the hybridized oligonucleotide paints is performed by heat activation of the targeting moieties, light activation of the targeting moieties, or chemical activation of the targeting moieties or any combination thereof.

11. The method of claim 1, wherein the one or more targeting moieties are covalently attached to a protein, a peptide, a carbohydrate, a lipid, or a chemical moiety or any combination thereof.

12. The method of claim 11, wherein the chemical moiety is a methyl group or an acetyl group.

13. The method of claim 1, wherein the one or more factors are selected from the group consisting of histone proteins, scaffold proteins, transcription factors, DNA binding proteins, DNA repair factors, and nucleases or any combination thereof.

14. The method of claim 1, wherein the chromosome is within a cell from the biological sample.

15. The method of claim 1, wherein the oligonucleotide paints are ligated oligonucleotide paints.

16. The method of claim 1, wherein the oligonucleotide paints are hapten-conjugated oligonucleotide paints.

17. The method of claim 1, wherein the oligonucleotide paints unbound to the different chromosomal regions of the chromosome are removed by washing a support having the biological sample immobilized on the support.

18. The method of claim 17, wherein the different chromosomal regions are present in single or low copy numbers.

19. The method of claim 1 wherein one of the one or more targeting moieties is a protein capture moiety, a lipid capture moiety, a sugar capture moiety or a nucleic acid capture moiety.

20. The method of claim 1 wherein one of the one or more targeting moieties is

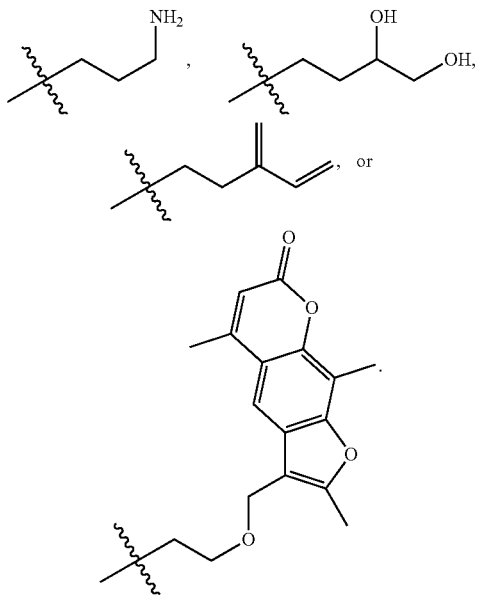

21. The method of claim 1 wherein the plurality of oligonucleotide paints comprises a set of oligonucleotide paints bound to a plurality of sub-chromosomal regions.

22. The method of claim 21 wherein the plurality of sub-chromosomal regions comprises at least 50 regions.

23. A method for identifying one or more factors bound to one or more targeting moieties of a plurality of oligonucleotide paints in a biological sample by in situ hybridization, comprising the steps of:

hybridizing the plurality of oligonucleotide paints to different regions of genomic DNA or mitochondrial DNA in the biological sample by in situ hybridization, thereby forming hybridized oligonucleotide paints, wherein each of the oligonucleotide paints comprises a 5' primer sequence, a nucleotide sequence capable of hybridizing to a specific region of the genomic DNA or the mitochondrial DNA, 3' primer sequence, and one or more targeting moieties, and the nucleotide sequence capable of hybridizing to the specific region of the genomic DNA or the mitochondrial DNA is located between the 5' primer sequence and the 3' primer sequence and is different in each of the oligonucleotide paints and the 5' primer sequence and the 3' primer sequence comprises either nucleotide sequences of a universal primer or nucleotide sequences fully complementary to the universal primer;

removing the oligonucleotide paints unbound to the different regions of the genomic DNA or the mitochondrial DNA from the hybridized oligonucleotide paints;

covalently attaching the targeting moieties of the hybridized oligonucleotide paints to the one or more factors in the biological sample; and identifying the one or more factors bound to the one or more targeting moieties of the plurality of oligonucleotide paints in the biological sample by identifying the factors attached to the targeting moieties of the hybridized oligonucleotide paints.

24. The method of claim 23, wherein the one or more factors are selected from the group consisting of a protein, a peptide, a carbohydrate, a lipid, and a chemical moiety or any combination thereof.

25. A method for identifying one or more factors bound to one or more targeting moieties of a plurality of oligonucleotide paints in a biological sample by in situ hybridization, comprising the steps of:

hybridizing the plurality of oligonucleotide paints to different regions of genomic DNA or mitochondrial DNA in the biological sample by in situ hybridization, thereby forming hybridized oligonucleotide paints, wherein the plurality of oligonucleotide paints has retrievable moieties, and wherein each of the oligonucleotide paints comprises a 5' primer sequence, a nucleotide sequence capable of hybridizing to a specific region of the genomic DNA or the mitochondrial DNA, 3' primer sequence, and one or more targeting moieties, and the nucleotide sequence capable of hybridizing to the specific region of the genomic DNA or the mitochondrial DNA is located between the 5' primer sequence and the 3' primer sequence and is different in each of the oligonucleotide paints and the 5' primer sequence and the 3' primer sequence comprises either nucleotide sequences of a universal primer or nucleotide sequences fully complementary to the universal primer;

removing the oligonucleotide paints unbound to the different regions of the genomic DNA or mitochondrial DNA from the hybridized oligonucleotide paints;

covalently attaching the targeting moieties of the hybridized oligonucleotide paints to the one or more factors in the biological sample; and identifying the one or more factors bound to the one or more targeting moieties of the plurality of oligonucleotide paints in the biological sample by identifying the factors attached to the targeting moieties of the hybridized oligonucleotide paints.

26. The method of claim 25, wherein the one or more factors are selected from the group consisting of a protein, a peptide, a carbohydrate, a lipid, and a chemical moiety or any combination thereof.

* * * * *